United States Patent [19]

Laruelle et al.

[11] Patent Number: 4,472,387
[45] Date of Patent: Sep. 18, 1984

[54] PHARMACEUTICAL COMPOSITIONS CAPABLE OF INCREASING CEREBRAL SEROTONIN CONCENTRATION

[75] Inventors: Claude Laruelle, Villeneuve-Loubet; Marcel Lepant, Vence, both of France

[73] Assignee: Panmedica S.A., Carros, France

[21] Appl. No.: 418,599

[22] Filed: Sep. 16, 1982

[30] Foreign Application Priority Data

Sep. 16, 1981 [FR] France ................ 81 17492
Nov. 8, 1982 [FR] France ................ 82 13980

[51] Int. Cl.$^3$ .............. A61K 31/52; A61K 31/70; A61K 31/195; A61K 31/455
[52] U.S. Cl. .................. 424/180; 424/253; 424/266; 424/319
[58] Field of Search ............ 424/180, 319, 253, 266

[56] References Cited

FOREIGN PATENT DOCUMENTS 2841170 4/1980 Fed. Rep. of Germany .
2081539 2/1971 France .
1535778 12/1978 United Kingdom .

OTHER PUBLICATIONS

Martin Negwer, "Organisch-Chemische Arzneimittel und ihre Synonyma", 5e Edition, vol. II, 1978, Akademie-Verlag Berlin (DE), No. 6249, 5-Hydroxytryptophan.

Primary Examiner—Stanley J. Friedman
Attorney, Agent, or Firm—Oblon, Fisher, Spivak, McClelland & Maier

[57] ABSTRACT

A pharmaceutical composition suitable for increasing cerebral serotonin concentration, comprising a serotonin precursor selected from the group consisting of 5-hydroxytryptophan and derivatives of 5-hydroxytryptophan having the formula:

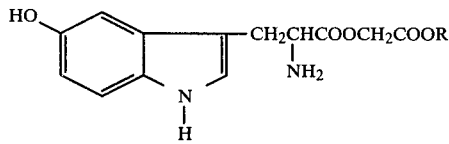

wherein R represent hydrogen; a $C_1$–$C_{12}$ alkyl group; or a $C_5$–$C_{16}$ alicyclic, monocyclic aromatic hydrocarbyl, or polycyclic aromatic hydrocarbyl group; and a nitrogenous heterocyclic compound selected from the group consisting of inosine, theophylline, theobromine, allopurinol, pyridoxine, hypoxanthine, folic acid, adenine, nicotinamide, caffeine, and orotic acid.

7 Claims, No Drawings

PHARMACEUTICAL COMPOSITIONS CAPABLE OF INCREASING CEREBRAL SEROTONIN CONCENTRATION

BACKGROUND OF THE INVENTION

1. Field of the Invention

The present invention relates to novel pharmaceutical compositions containing 5-hydroxytryptophane or a derivative of 5-hydroxytryptophane.

2. Description of the Prior Art

The importance of the role of serotonin (5-hydroxytryptamine) as a cerebral intercellular chemical mediator is known (cf. particularly applicant's French Patent Application No. 81-01931). For example, serotonin deficiency conditions cause certain disorders of sleep, depression syndromes and phenylketonuria. The administration of 5-hydroxytryptophane (5-HTP), a direct precursor of serotonin, compensates for this deficiency since serotonin is synthesized from ingested tryptophane according to the following metabolic chain:

tryptophane→5-hydroxytryptophane→5-hydroxy-tryptamine

The administration of 5-HTP is in fact preferable to the administration of a monoamine oxidase inhibitor, which blocks the degradation of both serotonin and other biogenic amines and is therefore sometimes used to increase blood concentrations of serotonin.

Nonetheless, the administration of 5-HTP as an immediate precursor of serotonin presents a considerable drawback: the overall yield of cerebral serotonin actually synthesized with respect to the amount of 5-hydroxytryptophane administered is very low. This conversion level is very low for various reasons; among others, it is due to mediocre passage of the gastrointestinal and hematoencephalic barriers by 5-HTP, considerable decarboxylation of 5-hydroxytryptophane at the peripheral level and high hepatic catabolism of 5-HTP. This loss can be partly compensated for by the simultaneous administration of a peripheral decarboxylase inhibitor, but this addition has other drawbacks.

Accordingly, there remains a need for pharmaceutical compositions containing 5-hydroxytryptophane which overcome these previously known defieciencies.

SUMMARY OF THE INVENTION

It is an object of this invention to provide a pharmaceutical composition containing 5-hydroxytryptophane which is more efficient in increasing cerebral intercellular serotonin levels than 5-hydroxytryptophane administered alone.

This and other objects of the invention as will hereinafter become more readily apparent have been accomplished by providing a pharmaceutical composition suitable for increasing cerebral serotonin concentration, comprising:

a serotonin precursor selected from the group consisting of 5-hydroxytryptophane and derivatives of 5-hydroxytryptophane having the formula

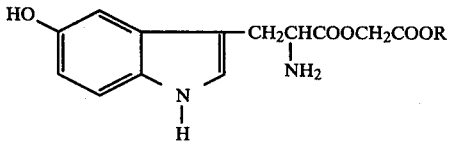

wherein R represents hydrogen; a $C_1$–$C_{12}$ alkyl group; or a $C_5$–$C_{16}$ alicyclic hydrocarbyl, monocyclic aromatic hydrocarbyl or polycyclic aromatic hydrocarbyl group; and a nitrogenous heterocyclic compound selected from the group consisting of inosine, theophyllin, theobromine, allopurinol, pyridoxine, hypoxanthine, folic acid, adenine, nicotinamide, caffeine and orotic acid.

DESCRIPTION OF THE PREFERRED EMBODIMENTS

In the first phase of their research leading to the present invention (cf. French Patent No. 81-01931 already mentioned, which is herein incorporated by reference), the applicants developed derivatives of 5-HTP corresponding to the following general formula I:

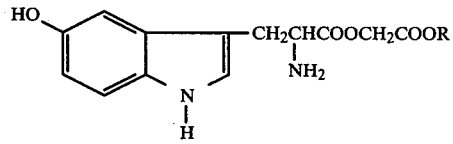

in which: R represents a hydrogen atom; an alkyl group contains 1 to 12 carbon atoms; or an alicyclic, monocyclic aromatic or polycyclic aromatic hydrocarbyl group containing 5 to 16 carbon atoms. These derivatives enable the endogenous serotonin level in the brain to be considerably increased over the levels obtainable with the same amount of 5-HTP itself.

Examples of compounds in which R is a $C_1$–$C_{12}$ alkyl group include those in which R is methyl, propyl, pentyl, octyl or dodecal. Any alkyl group having 3 or more carbons may be straight-chained or branched, for example, n-butyl, iso-butyl and t-butyl. Alicyclic R groups of the contemplated scope include cyclopentyl, cyclohexyl, decalinyl, and perhydroanthryl, including cyclic radicals attached to the oxygen of the given formula by an divalent alkyl linking group as well as cyclic radicals which have alkyl substituents, such as the 4-methyl-cyclohexyl radical. Monocyclic aromatic hydrocarbyl groups include the phenyl group and its alkyl substitution products, such as p-isopropyl-phenyl, as well as phenyl groups attached to the 5-HTP moiety through a divalent alkyl linking group, such as benzyl and alkyl-substituted benzyl groups. Polycyclic aromatic hydrocarbyl groups contemplated include naphthyl, anthryl, and phenanthryl groups and their alkyl substitution products as well as such radicals linked to the 5-HTP moiety through a divalent alkyl linking group.

Compounds possessing substantially the same properties as 5-HTP and its derivatives defined by the above formula, which can be prepared in the same manner and are equivalent thereof, include but are not limited to those in which the 5-HTP molecule bears one or more $C_1$–$C_3$ alkyl, halo, or hydroxyl group, or one or more similar small organic radical; those in which a different chalcogen replaces one of the oxygen atoms; and those in which the group —CH₂COOR is replaced by R or a similar group. Non-toxic salts of the compounds mentioned herein are also considered to be equivalents.

Through further research in this field, the applicants developed other compositions and complexes based on 5-HTP which not only reduce considerably the degradation of 5-HTP, but also suprisingly potentiate its effect.

It is known that the cyclic nucleotides participate in the mechanism of action of the neurotransmitters at the pre- and post-synaptic levels [cf. for example Greengard, Nature 260, 101 (1976)], and certain cyclic nucleotides, such as inosine and hypoxanthine can constitute endogenous ligands of receptors of benzodiazepines [P. Skolnick, Proc. Natl. Acad, Sci. USA, 76, 1515-18 (1979)].

The present invention provides novel pharmaceutical compositions capable of correcting the deficiencies of serotonin metabolism which are characterized in that they comprise an association of 5-HTP or a derivative thereof with derivatives of purine, pyrimidine, or pyridine bases, or with a combination of derivatives of these bases.

The applicants have in fact observed that the combination of 5-HTP with a purine, pyridine, or pyrimidine heterocyclic base enables the cerebral levels of 5-HTP, serotonin and 5-hydroxyindolacetic acid (5-HIAA), which is the principal metabolite of serotonin, to be considerably increased.

The presence of the purine, pyridine, or pyrimidine bases modifies the enzymatic mechanism of degradation of 5-HTP by 5-hydroxytryptophane decarboxylase (present in the kidney, liver and stomach), which enables the amount of 5-HTP administered during treatment, intended to compensate for the reduction in cerebral serotonin, to be considerably reduced.

The pharmaceutical composition of the invention preferentially comprises 5 to 95% of 5-hydroxytryptophane or a derivative of 5-hydroxytryptophane having the previously mentioned formula and 95 to 5% of a nitrogenous heterocyclic derivative of a purine, pyrimidine, or pyridine base as active ingredients. According to an advantageous embodiment of the present invention, 5-HTP is chemically associated with the nitrogenous heterocyclic base. It is particularly preferred that this asociation be an equimolar association. This association may be either in the form of a complex or a salt of 5-HTP with the purine, pyrimidine, or pyridine bases.

According to the invention, the 5-HTP may be used in the form of any one of its enantiomers: the (L) form, the (D) form, or the racemic mixture (DL).

Among the nitrogenous heterocyclic rings, the following derivatives are particularly preferred for their potentiating effect on the serotoninergic activity of the 5-HTP: inosine, theophyllin, theobromine, allopurinol, pyridoxine, hypoxanthine, folic acid, adenine, nicotinamide, caffein, and ozotic acid.

Other nitrogenous heterocyclic compounds which are derivatives of purine, pyrimidine, or pyridine bases are contemplated to likewise potentiate the activity of 5-HTP or its derivatives when administered therewith and will likewise reduce the required amount of the 5-HTP derivative being administered. Typical equivalent compounds include but are not limited to purine, pyrimidine, and pyridine rings substituted with the same substituents or homologs or analogs of the substituents of the specific nitrogenous bases listed immediately above.

In interpreting the clinical results of these remarkable medicaments, the applicants have observed that a complex of inosine with 5-HTP, particularly a complex of inosine with (L)-5-HTP, triples the blood levels of 5-HTP and 5-hydroxyindolacetic acid (5-HIAA), the principal metabolite of serotonin. The reduction in administration of 5-HTP made possible by these complexes is interesting not only from the economic point of view but also from an important clinical advantage, since prolonged administration of high doses of 5-HTP often results in renal lesions.

This excellent pharmacological response of the complex of inosine with (L)-5-HTP and the almost entire absence of activity of (D)-5-HTP has led the applicants to study a novel, simple, and economic process for the preparation of the complex of inosine with (L)-5-HTP from a racemic industrial product; namely, (DL)-5-HTP.

Known processes for separating optically active isomers from a racemic mixture of an amino acid involve expensive techniques and reagents. Thus, for example, isolation of (L)-5-hydroxytryptophane from a racemic mixture by the method of Kyowa Hakko Kogyo (Japanese Patent No. 75-58-061) involves a reaction with D-threo-1-(paranitrophenyl)-2-amino-1,3-propanediol. The L-isomer of the latter reagent is also used by Sankyo (Japanese Patent No. 73-91063) to separate the diastereoisomers of (DL)-5-HTP after blocking the reactive functions. Rinderknecht [Helv. Chim. Acth., 47 (8), 2403] uses successively quinine and quinidine to separate the two diastereoisomers.

All the techniques of the prior art hence recognize blocking of the reactive functions of (DL)-5-HTP, reacting with an optically active derivative, separating the pairs of diastereoisomers, and then finally unblocking the protective groups. This set of operations is long and expensive.

Consequently, a further object of the present invention is to provide a process for the preparation of the complex of inosine with (L)-5-HTP which responds to the necessities of practice better than previously known processes, particularly in that it eliminates the prior preparation of the (L) derivative.

It is also an object of the present invention to provide a process for making a practically pure inosine-(L)-5-HTP complex. In this process, equimolecular amounts of inosine, for example, directly from a commercial source, and (DL)-5-HTP in aqueous solution are reacted at 60°-80° C., preferably at 70° C.; the reaction mixture is allowed to cool slowly for 3 to 7, preferably 5, hours to ambient temperature i.e., about 20°-30° C.; and then maintained for 36 to 72, preferably about 48, hours at 1°-10° C., preferable close to 5° C. The pure crystals of the complex of inosine with (L)-5-HTP are then separated.

The mother-liquors obtained after the separation of the (L)-5-HTP crystals are enriched in (D)-5-HTP. This may be racemized in order to obtain a higher yield of (L)-5-HTP. Racemization may be accomplished by, for example, taking the mother-liquors remaining after the filtration of the crystals of inosine with (L)-5-HTP to a temperature of between 150° and 200° C. for 3 to 5 hours. It is preferred to isolate the 5-HTP crystals present in the mother-liquors from inosine by passing the mother-liquors over an ion exchange resin of the strong acid type, followed by elution with a dilute solution of hydrazine hydrate. This method of purification followed by racemization enables one to avoid the high coloration caused by heating of inosine.

The pharmaceutical composition of the present invention may be used to treat any mammal suffering from a deficiency of cerebral serotonin. Humans are the primary mammal for which this pharmaceutical preparation is intended.

Treatment consists of administering to a mammal having a lower than normal cerebral serotonin level an amount of a pharmaceutical composition of the present invention effective to increase the cerebral serotonin level. A suitable regime involves administering a low initial dose followed by monitoring of the serotonin or 5-HIAA level. Larger dosages may be given later if the low dose does not prove effective. For humans, administration of 1–50 mg/kg is a suitable starting dose. About 25 mg/kg is preferred. Monitoring of serotonin levels may be accomplished by clinical observation rather than laboratory testing if desired; i.e., the patient may be observed for the elimination of sleep disorder, depression, etc. Daily dosages of 1 to 100 mg/kg are preferred.

Although oral administration is preferred, the pharmaceutical compositions of the present invention may be administered by intramuscular injection, intravenous injection, and tubal feeding, either gastric or intestinal. The pharmaceutical compositions of the invention may comprise in addition to the active ingredients 5–95% of a non-toxic pharmaceutical carrier, including both solids and liquids, such as talc, sucrose, isotonic aqueous solutions, and water, in the form of a tablet, capsule, solution, or emulsion.

Having generally described the invention, a more complete understanding can be obtained by reference to certain specific examples, which are provided herein for purposes of illustration only and are not intended to be limiting unless otherwise specified.

EXAMPLES OF THE PREPARATION OF PHARMACEUTICAL COMPOSITIONS OF THE INVENTION

EXAMPLE 1: (L)-5-HTP INOSINATE 134 g of inosine and 110 g of (DL)-5-HTP were added to 20 liters of water at 70° C. The temperature of the reaction mixture was allowed to cool for 5 hours to room temperature. Crystallization started spontaneously and was then continued by cooling to 5° C. for 48 hours. The crystals were filtered at +5° C. and washed twice with 500 ml of ice water. After drying, the pure equimolecular complex of inosine-(L)-5-HTP (in the form of monohydrated crystals) was obtained with a yield of 83% calculated with respect to the (L)-diastereoisomer present in the starting racemic 5-HTP.

The characteristics of the product obtained were:
$[\alpha]_D^{25} = 37.7°$ (C=0.2, water).
melting point: 191° C.
water content (Karl Fischer)=3.5%.

The quantative determination of the constituents by high performance liquid chromatography indicates:
5-HTP=43.5%.
Inosine=53%.
Elementary analysis of the elements C, H, and N agrees with the composition: Inosine-5-HTP-1H$_2$O.

The optical purity of the complex (determined after isolatin of the 5-HTP on a cationic resin) was greater than 98%.

EXAMPLE 2: (DL) 5-HYDROXYTRYPTOPHANE INOSINATE 22 g (0.1 mole) of (DL)-5-hydroxytryptophane was dissolved in the minimum amount of distilled water at 50° C. (namely, about 1 liter), and 27 g (0.1 mole) of inosine (or 9-$\beta$-D-ribofuranosylhypoxanthine) was added. After cooling, the compound was filtered off. It crystallized with one molecule of water (m.p. 195° C.)

Elementary analysis: calculated: C=49.80%, H=5.14%, N=16.60%; found: C=50%, H=5.10%, N=16.43%.

EXAMPLE 3: THEOPHYLLINE SALT OF (DL) 5-HYDROXYTRYPTOPHANE

In 2 liters of distilled water, 11.0 g (0.05 mole) of (DL)-hydroxytryptophane and 9.0 g (0.05 mole) of theophylline (3,7-dihydro-1,3-dimethyl-1-H-purine-2,6-dione) were dissolved. After several hours of refrigeration, crystals formed. These were filtered and dried under vacuum protected from light (m.p. 265° C.). Aqueous solubility at 20° C.=0.1%.

Elementary analysis: calculated: C=55.38%, H=5.13%, N=21.5%; found: C=55.45%, H=5.07%, N=21.7%.

EXAMPLE 4: THEOPHYLLINE SALT OF (L)-5-HYDROXYTRYPTOPHANE 0.05 mole, namely 9.0 g, of theophylline and 0.05 mole, namely 11 g, of (L)-5-hydroxytryptophane were dissolved in about 2 liters of water. After several days of refrigeration, the crystals formed were filtered and dried protected from light (m.p. 265° C.) Aqueous solubility at 20° C. was 0.35%.

EXAMPLE 5: EQUIMOLECULAR COMPLEX OF (L)-5-HYDROXYTRYPTOPHANE AND OF ALLOPURINOL

In a minimum amount of boiling water, 2.2 g (0.01 mole) of (L)-5-hydroxytryptophane and 1.4 g of allopurinol (4-hydroxypyrazolo-(3,4-d)-pyridimidine; 0.01 mole) were dissolved. After cooling and several days of refrigeration, the crystals formed were filtered and dried protected from light (mp>290° C.)

Elementary analysis: calculated: C=53.3%, H=5.5%, N=23.3%, O=17.8%; found: C=53.1%, H=5.7%, N=23.3%, O=18%.

EXAMPLE 6: EQUIMOLECULAR COMPLEX OF PYRIDOXINE WITH (DL)-5-HYDROXYTRYPTOPHANE

Equimolecular amounts of (DL)-5-HTP and pyridoxine hydrochloride (5-hydroxy-6-methyl-3,4-hydroxymethylpyridine) were dissolved in a minimum of water (namely, about 15 liters per mole). After evaporation of the water, the residue was taken up again with alcohol. In this way 90% of the well-crystallized equimolecular complex was obtained: m.p.=175° C., very soluble in water.

EXAMPLE 7: EQUIMOLECULAR COMPLEX OF PYRIDOXINE WITH (L)-5-HYDROXYTRYPTOPHANE

Under the conditions of Example 6 above, (L)-5-HTP and pyridoxine hydrochloride were dissolved. After taking up again in alcohol the residue from the evaporation, 90% of the well-crystallized equimolecular complex were obtained: m.p. 165° C. and $[\alpha]_D^{25} = -9°$ (0.2% water).

Elementary analysis: calculated: C=53.58%, H=5.64%, N=9.8%, Cl=8.34%; found: C=53.50%, H=5.42%, N=9.62%.

EXAMPLE 8: EQUIMOLECULAR COMPLEX OF HYPOXANTHINE WITH (L)-5-HYDROXYTRYPTOPHANE 13.6 g (0.1 mole) of hypoxanthine (1,7-dihydropurine-6-one) was dissolved in a liter of boiling water, and 22.0 g (0.1 mole) of (L)-5-hydroxytryptophane was added. The solution was immediately concentrated under reduced pressure, and the dry residue was taken up again with hot ethanol and then dried. An equimolecular complex of hypoxanthine and (L)-5-hydroxytryptophane was obtained.

Elementary analysis: calculated: C=53.3%, H=5.5%, N=23.3%, O=17.8%; found: C=53.5%, H=5.5%, N=23.3%, O=17.6%.

EXAMPLE 9: EQUIMOLECULAR ASSOCIATION OF (L)-5-HYDROXYTRYPTOPHANE AND FOLIC ACID 11 g of (L)-5-hydroxytryptophane and 22 g of folic acid (N-[4-(2-amino-1,4-dihydro-4-oxo-6-pteridinyl)methylaminobenzoyl]-L-glutamic acid) were carefully mixed and checked by suitable techniques for the homogeneity of the mixture.

EXAMPLE 10: NICOTINAMIDE SALT OF (L)-5-HYDROXYTRYPTOPHANE 22.0 g (0.1 mole) of (L)-5-hydroxytryptophane was suspended in 200 ml of water at 50° C., and 12.2 g (0.1 mole) of nicotinamide was added. The products passed rapidly into solution. The solution was evaporated under vacuum; and after drying, the desired derivative was obtained.

Elementary analysis: calculated: C=59.6%, H=5.2%, N=1.64%, O=18.7%; found: c=59.5%, H=5.3%, N=16.4%, O=18.5%.

EXAMPLE 11: THEOBROMINE SALT OF (L)-5-HYDROXYTRYPTOPHANE 9.0 g (0.05 mole) of theobromine (3,7-dihydro-3,7-dimethyl-1H-purine-2,6-dione) and 11 g (0.05 mole) of (L)-5-hydroxytryptophane were dissolved in 500 ml of hot water. The solution was cooled; and after several days at 0° C., the crystals formed were filtered off and dried under vacuum [mp.>250° C. (dec)—monohydrated crystals].

Elementary analysis: calculated: C: 54.0%, H=5.0%, N=21%, O=20%; found: C: 54.2%, H=5.1%, N=21%, O=12.8%.

EXAMPLE 12: CAFFEINE SALT OF (L)-5-HYDROXYTRYPTOPHANE 10 g (0.05 mole) of caffeine (1,3,7-trimethyl-2,6-dioxopurine) and 11 g (0.05 mole) of (L)-5-hydroxytryptophane were dissolved in 200 ml of water at 80° C. The solution was cooled; and after several days at 0° C., the crystals formed were filtered and dried under vacuum.

Elementary analysis: calculated: C=55.1%, H=5.3%, N=20.3%, O=19.3%; found: C=55%, H=5.2%, N=20.3%, O=19.5%.

ACCOUNT OF THE PHARMACOLOGICAL STUDY

This study, carried out in the rat, determined the efficacy of the compositions according to the present invention on the cerebral metabolism of serotonin and established the potentiation of the serotoninogenic effect with respect to the reference (L)-5-HTP. (Purine, pyrimidine, and pyridine bases are, of themselves, entirely devoid of this activity.)

The animals were male adult rats of the OFA stain weighing 160 to 180 g. They were subjected to an alternating light cycle of 12 hours of light and 12 hours of darkness.

The various derivatives according to the invention were administered in distilled water intragastically at doses of 10, 25, and 50 mg/kg. After one hour, the rats were decapitated; and the contents of 5-hydroxytryptamine (5-HT), of 5-HIAA, and of 5-hydroxytryptophane in the brains were determined by the methods published by G. Curzon and Cool, [Brit. J. Pharmaco., 39, 653 (1970)].

The results of these determinations are collected in Table I below. They represent the percentage increase of cerebral endogenic levels at 10, 25, 50 mg/kg of the pure (L)-5-HTP (control) and of compositions according to the present invention for a given batch of control rats.

TABLE 1

| Composition | Percent Increase in Cerebral Endogenic Level of Indicated Substance After Administration of Pharmaceutical Composition at Indicated Rate ||||||||||||
| | (L)-5-HTP ||| 5-HT ||| 5-HIAA ||| 5-Ht + 5-HIAA |||
| | 10 mg/kg | 25 mg/kg | 50 mg/kg | 10 mg/kg | 25 mg/kg | 50 mg/kg | 10 mg/kg | 25 mg/kg | 50 mg/kg | 10 mg/kg | 25 mg/kg | 50 mg/kg |
|---|---|---|---|---|---|---|---|---|---|---|---|---|
| (L)-5-HTP pure | 120 | 260 | 650 | 10 | 25 | 35 | 40 | 110 | 300 | 55 | 110 | 180 |
| Example 1 | 135 | 1755 | 2665 | 2 | 100 | 70 | 165 | 290 | 1010 | 100 | 195 | 545 |
| Example 2 | 110 | 1665 | 1955 | 2 | 80 | 110 | 135 | 345 | 1190 | 85 | 220 | 700 |
| Example 3 | 35 | 780 | 870 | — | 20 | 4 | 60 | 175 | 285 | 35 | 100 | 160 |
| Example 4 | 55 | 1200 | 1710 | — | 25 | 35 | 85 | 270 | 870 | 75 | 150 | 490 |
| Example 6 | 115 | 230 | 1575 | — | 30 | 60 | 20 | 90 | 360 | 8 | 65 | 210 |
| Example 7 | 190 | 420 | 2500 | 20 | 80 | 25 | 35 | 230 | 755 | 40 | 165 | 390 |
| Example 5 | 108 | 830 | 2100 | 15 | 70 | 115 | 90 | 100 | 765 | 60 | 85 | 475 |
| Example | 180 | 1700 | 2820 | — | 35 | 140 | 190 | 220 | 1190 | 110 | 130 | 720 |

TABLE 1-continued

| Composition | Percent Increase in Cerebral Endogenic Level of Indicated Substance After Administration of Pharmaceutical Composition at Indicated Rate | | | | | | | | | | | |
|---|---|---|---|---|---|---|---|---|---|---|---|---|
| | (L)-5-HTP | | | 5-HT | | | 5-HIAA | | | 5-Ht + 5-HIAA | | |
| | 10 mg/kg | 25 mg/kg | 50 mg/kg | 10 mg/kg | 25 mg/kg | 50 mg/kg | 10 mg/kg | 25 mg/kg | 50 mg/kg | 10 mg/kg | 25 mg/kg | 50 mg/kg |
| 9 | | | | | | | | | | | | |

The foregoing study demonstrates that the compositions according to the present invention enable a considerable economy in 5-HTP to be realized and the effects of the latter to be remarkably potentiated: this improvement is on the average between 200% and 300% and can even reach 500%.

TOXICITY OF THE COMPOSITIONS ACCORDING TO THE PRESENT INVENTION

The toxicities of the salts and the complexes of 5-HTP according to the present invention are very low as witnessed by the $LD_{50}$'s per os/mice assembled in Table 2 below:

TABLE 2

| | Product of Example 10 | Product of Example 4 | Product of Example 12 | Product of Example 9 | Product of Example 5 |
|---|---|---|---|---|---|
| $LD_{50}$ per os (mg/kg) | >2000 | 1000 | >2000 | 1000 | 1000 |

The advantage of compositions according to the present invention is immediately established by the considerable increase in the therapeutic index, which has the double advantage of improving the response on the therapeutic level and reducing the cost of the treatment by the economy realized in the reduced dosage of the 5-HTP.

The invention now being fully described, it will be apparent to one of ordinary skill in the art that many changes and modifications can be made thereto without departing from the spirit or scope of the invention as set forth herein.

What is claimed as new and desired to be secured by Letters Patent of the United States is:

1. A pharmaceutical composition suitable for increasing cerebral serotonin concentration, comprising:
    5-95% of a serotonin precursor selected from the group consisting of 5-hydroxytryptophan and derivatives of 5-hydroxytryptophan having the formula:

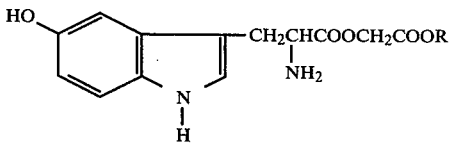

wherein
   R represent hydrogen; a $C_1$-$C_{12}$ alkyl group; or a $C_5$-$C_{16}$ alicyclic, monocyclic aromatic hydrocarbyl, or polycyclic aromatic hydrocarbyl group; and
   95-5% of a nitrogenous heterocyclic compound selected from the group consisting of inosine, theophylline, theobromine, allopurinol, hypoxanthine, adenine, nicotinamide, and caffeine.

2. The pharmaceutical composition of claim 1, wherein said serotonin precursor is 5-hydroxytryptophane.

3. The pharmaceutical composition of claim 1, wherein said serotonin precursor and said heterocyclic compound are present in equal molar amounts.

4. The pharmaceutical composition of claim 1, wherein said serotonin precursor and said heterocyclic compound form a complex.

5. The pharmaceutical composition of claim 1, wherein said serotonin precursor and said heterocyclic compound form a salt.

6. The pharmaceutical composition of claim 1, wherein said serotonin precursor is (L)-5-hydroxytryptophane or a derivative of (L)-5-hydroxytryptophane having said formula.

7. The pharmaceutical composition of claim 6, wherein said heterocyclic compound is inosine.

* * * * *